(12) United States Patent
Dupuis

(10) Patent No.: US 6,703,026 B2
(45) Date of Patent: Mar. 9, 2004

(54) COSMETIC COMPOSITION CONTAINING A POLYORGANOSILOXANE AND AN ACRYLIC TERPOLYMER, AND USE OF THIS COMPOSITION FOR TREATING KERATINOUS MATERIAL

(75) Inventor: Christine Dupuis, Paris (FR)

(73) Assignee: L'Oreal, Paris (FR)

( * ) Notice: Subject to any disclaimer, the term of this patent is extended or adjusted under 35 U.S.C. 154(b) by 239 days.

(21) Appl. No.: 09/332,003

(22) Filed: Jun. 14, 1999

(65) Prior Publication Data

US 2002/0061284 A1 May 23, 2002

(30) Foreign Application Priority Data

Jun. 15, 1998 (FR) ............................. 98 07512

(51) Int. Cl.⁷ ............................. A61K 7/00; A61K 7/42
(52) U.S. Cl. .................. 424/401; 424/59; 424/400; 514/861; 514/863; 514/864; 514/937
(58) Field of Search .................. 424/401, 59; 514/861, 514/863, 864, 937

(56) References Cited

U.S. PATENT DOCUMENTS

| | | |
|---|---|---|
| 4,514,552 A | 4/1985 | Shay et al. |
| 5,015,711 A | 5/1991 | Simonet et al. ............. 526/301 |
| 5,063,051 A | 11/1991 | Grollier et al. |
| 5,066,710 A | 11/1991 | Simonet et al. ............. 524/555 |
| 5,262,087 A | 11/1993 | Tachibana et al. |
| 5,292,843 A | 3/1994 | Jenkins et al. ........... 526/318.5 |
| 5,294,693 A | 3/1994 | Egraz et al. ................ 526/310 |
| 5,362,415 A | 11/1994 | Egraz et al. ........... 252/174.24 |
| 5,573,709 A | 11/1996 | Wells |
| 5,599,800 A | 2/1997 | Candau et al. |
| 5,620,684 A | 4/1997 | Dupuis |
| 5,637,306 A | 6/1997 | Cauwet et al. |

FOREIGN PATENT DOCUMENTS

| | | |
|---|---|---|
| EP | 0173109 | 3/1986 |
| EP | 0350414 | 1/1990 |
| EP | 0 521 748 A1 | 1/1993 |
| EP | 0577526 | 1/1994 |
| EP | 0 824 914 | 2/1998 |
| EP | 0 875 557 A2 | 11/1998 |
| FR | 2 740 037 | 12/1997 |
| HU | 215485 | 2/1997 |
| HU | 215636 | 2/1997 |
| HU | 216585 | 2/1997 |
| HU | P9301659 | 2/1997 |
| HU | P9600137 | 2/1997 |
| WO | 93/10162 | 6/1992 |
| WO | 93/08787 | 5/1993 |
| WO | WO93/24544 | 12/1993 |

OTHER PUBLICATIONS

Neumüller, Römpps Chemie–Lexikon, Achte, neubearbeitete und erweiterte Auflage, Franckh'sche Verlagshandlung Stuttgard, pp. 3855–3856.

Primary Examiner—Shelley A. Dodson
(74) Attorney, Agent, or Firm—Nixon & Vanderhye, P.C.

(57) ABSTRACT

The present application relates to cosmetic compositions containing, in a cosmetically acceptable aqueous medium, at least one polyorganosiloxane and an acrylic terpolymer, as well as to the use of these compositions for treating keratinous material, in particular the skin or the hair. The acrylic terpolymer comprises:

a) about 20 to 70% by weight of a carboxylic acid containing α,β-monoethylenic unsaturation;

b) about 20 to 80% by weight of a non-surfactant monomer containing monoethylenic unsaturation, which is different from a), and c) about 0.5 to 60% by weight of a nonionic urethane monomer which is the product of reaction of a monohydric nonionic surfactant with a monoisocyanate containing monoethylenic unsaturation. The polyorganosiloxane is preferably a non-volatile silicone.

33 Claims, No Drawings

COSMETIC COMPOSITION CONTAINING A POLYORGANOSILOXANE AND AN ACRYLIC TERPOLYMER, AND USE OF THIS COMPOSITION FOR TREATING KERATINOUS MATERIAL

The present invention relates to cosmetic compositions containing, in combination, at least one polyorganosiloxane and an acrylic terpolymer, as well as to the use of these compositions for treating keratinous material.

Silicones are cosmetic products which are particularly sought for their conditioning properties and their softening and disentangling properties, in particular in hair formulations.

When certain silicones are used, such as those which are insoluble in aqueous medium, it is often necessary to introduce them in a thickened or gelled support in order to keep them in suspension and to obtain a stable composition.

It is also important to have available non-pasty, non-greasy compositions which spread well on the skin and the hair.

With the aim of obtaining a thickened or gelled support, thickening and/or gelling polymers are used. Gelling polymers are known which contain in their chain a hydrophilic part and a hydrophobic part consisting of a fatty chain, such as the product "Pemulen TR1" sold by the company Goodrich or the "Acrysol" polymers sold by the company Rohm & Haas. The polymer "Pemulen TR1" gives formulations of pasty texture which do not spread well. The polymer "Acrysol" does not have good gelling power and gives cloudy, unstable formulations.

The Applicant has discovered, surprisingly, that by using a novel family of thickening and/or gelling polymers and by combining them with polyorganosiloxanes, cosmetic formulations which have a satisfactory viscosity at a relatively low pH, which are stable, non-greasy, non-pasty and which spread well on the skin and the hair can be obtained.

The subject of the present invention is thus cosmetic compositions containing, in a cosmetically acceptable aqueous support, at least one polyorganosiloxane and an acrylic terpolymer which will be defined in greater detail later in the description.

This polymer makes it possible in particular to prepare rinse-out or leave-in, aqueous or aqueous-organic compositions containing cosmetically acceptable solvents, ranging from slightly gelled products to solid sticks or tubes.

The advantages of this terpolymer are that it is stable in electrolytic medium and has very good thickening power at a pH equal to or above 5.5, which allows a good level of viscosity to be achieved and allows high concentrations of alcohol to be used.

When used in combination with at least one polyorganosiloxane, this polymer makes it possible to prepare gelled, non-pasty products which are easy to spread, feel soft when applied and are stable on storage.

It also makes it possible to improve the conditioning effect of silicones on the hair, in particular their feel, their softness and their disentangling ability.

The acrylic terpolymer used in accordance with the invention is soluble or swellable in alkalis. It is characterized in that it comprises:

a) about 20 to 70% by weight, preferably 25 to 55% by weight, of a carboxylic acid containing α,β-monoethylenic unsaturation;

b) about 20 to 80% by weight, preferably 30 to 65% by weight, of a non-surfactant monomer containing monoethylenic unsaturation, which is different from a), and c) about 0.5 to 60% by weight, preferably 10 to 50% by weight, of a nonionic urethane monomer which is the product of reaction of a monohydric nonionic surfactant with a monoisocyanate containing monoethylenic unsaturation.

The carboxylic acid containing α,β-mono-ethylenic unsaturation a) can be chosen from many acids and in particular acrylic acid, methacrylic acid, itaconic acid and maleic acid. Methacrylic acid is preferred. A large proportion of acid is essential in order to give a polymer structure which dissolves and gives a thickening effect by reaction with an alkaline compound such as sodium hydroxide, alkanolamines, aminomethylpropanol or aminomethylpropanediol.

The terpolymer should also contain a large proportion, indicated above, of a monomer b) containing monoethylenic unsaturation which has no surfactant properties. The preferred monomers are those which give polymers that are water-insoluble when they are homopolymerized and are illustrated by $C_1$–$C_4$ alkyl acrylates such as methyl acrylate, ethyl acrylate and butyl acrylate, or corresponding methacrylates. The monomers more particularly preferred are methyl and ethyl acrylates. Other monomers which can be used are styrene, vinyltoluene, vinyl acetate, acrylonitrile and vinylidene chloride. Non-reactive monomers are preferred, such monomers being those in which the single ethylenic group is the only group which is reactive under the polymerization conditions. However, monomers which contain groups that are reactive under the action of heat can be used in certain situations, such as hydroxyethyl acrylate.

The monohydric nonionic surfactants used to obtain the nonionic urethane monomer c) are well known and are generally alkoxylated hydrophobic compounds containing an alkylene oxide forming the hydrophilic part of the molecule. The hydrophobes generally consist of an aliphatic alcohol or an alkylphenol in which a carbon chain containing at least six carbon atoms constitutes the hydrophobic part of the surfactant.

The preferred monohydric nonionic surfactants have the formula:

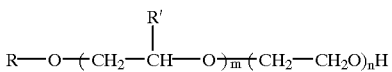

in which R is a $C_6$–$C_{30}$ alkyl or $C_8$–$C_{30}$ aralkyl group, R' is a $C_1$–$C_4$ alkyl group, n is an average number ranging approximately from 5 to 150 and m is an average number ranging approximately from 0 to 50, with the condition that n is at least as large as m and that n+m=5–150.

As preferred $C_6$–$C_{30}$ alkyl groups, mention may be made of dodecyl and $C_{18}$–$C_{26}$ alkyl radicals. As aralkyl groups, mention may be made more particularly of ($C_8$–$C_{13}$) alkylphenyl groups. The preferred group R' is the methyl group.

The monoisocyanate containing monoethylenic unsaturation which is used to form the nonionic urethane monomer c) can be chosen from a wide variety of compounds. A compound containing any copolymerizable unsaturation such as acrylic or methacrylic unsaturation can be used. An allylic unsaturation imparted by allyl alcohol can also be used. The preferred monoethylenic monoisocyanate is α,α-dimethyl-m-isopropenyl-benzylisocyanate.

The acrylic terpolymer defined above is obtained by aqueous emulsion copolymerization of the components a), b) and c) which is entirely common and described in patent application EP-A-0,173,109.

As terpolymers which can be used according to the invention, mention may be made of the products of reaction of methacrylic acid as component a), of ethyl acrylate as component b) and of a nonionic urethane macromonomer as component c), having the following structure:

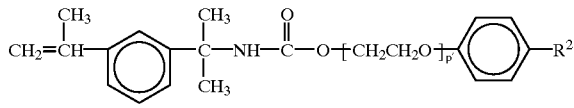

in which p' ranges from 6 to 150 and is preferably equal to 30 and $R^2$ is a $C_8$–$C_{13}$ alkyl radical, such as that described in Example 3 of patent application EP-A-0,173,109.

The preferred acrylic terpolymer used according to the invention is obtained from methacrylic acid as component a), methyl acrylate as component b) and a nonionic urethane macromonomer as component c), having the following structure:

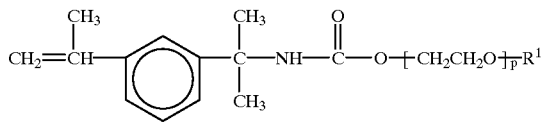

in which p ranges from 6 to 150 and $R^1$ is a $C_{18}$–$C_{26}$, alkyl radical preferably $C_{20}$–$C_{24}$, linear of plant origin, such as the docosyl radical.

The acrylic terpolymer is present in the cosmetic compositions of the invention in concentrations ranging from 0.01 to 20% by weight relative to the total weight of the composition, and preferably from 0.1 to 10% by weight.

The modified or non-modified polyorganosiloxanes used in the compositions according to the present invention are polyorganosiloxane oils or polyorganosiloxane gums or resins, in their natural state or in the form of solutions in organic solvents, or alternatively in the form of emulsions or microemulsions.

Among the polyorganosiloxanes used in accordance with the present invention, mention may be made, in a non-limiting manner, of:

I. Volatile Silicones

These have a boiling point of between 60° C. and 260° C. They are chosen from cyclic silicones containing from 3 to 7 and preferably 4 to 5 silicon atoms. They are, for example, octamethylcyclotetrasiloxane sold under the name "Volatile Silicone 7207" by Union Carbide or "Silbione 70045 V2" by Rhône-Poulenc, decamethylcyclopentasiloxane sold under the name "Volatile Silicone 7158" by Union Carbide, "Silbione 70045 V5 by Rhône-Poulenc, and mixtures thereof.

Mention is also made of cyclocopolymers of the dimethylsiloxane/methylalkylsiloxane type, such as "Volatile Silicone FZ 3109" sold by the company Union Carbide, which is a dimethylsiloxane/methyloctylsiloxane cyclocopolymer.

II. Non-volatile Silicones

These consist mainly of:
(i) polyalkylsiloxanes;
(ii) polyarylsiloxanes;
(iii) polyalkylarylsiloxanes;
(iv) silicone gums;
(v) silicone resins;
(vi) organomodified polyorganosiloxanes;
(vii) block copolymers having a polysiloxanepolyalkylene linear block as repeating unit;
(viii) grafted silicone polymers containing a non-silicone organic skeleton, consisting of an organic main chain formed from organic monomers not containing silicone, onto which is grafted, within the said chain as well as, optionally, on at least one of its ends, at least one polysiloxane macromonomer;
(ix) grafted silicone polymers containing a polysiloxane skeleton, grafted with non-silicone organic monomers, comprising a polysiloxane main chain onto which is grafted, within the said chain as well as, optionally, on at least one of its ends, at least one organic macromonomer containing no silicone;
(x) or mixtures thereof.

Among the polyalkylsiloxanes, mention may be made mainly of linear polydimethylsiloxanes containing trimethylsilyl end groups, such as, for example, and in a non-limiting manner, the "Silbione" oils of the 70047 series sold by Rhône-Poulenc; the oil "47 V 500 000" from Rhône-Poulenc or certain "Viscasil" oils from General Electric or "Mirasil" oils from Rhône-Poulenc, and linear polydimethylsiloxanes containing hydroxydimethylsilyl end groups, such as the oils of the 48 V series from Rhône-Poulenc.

In this class of polyalkylsiloxanes, mention may also be made of the polyalkylsiloxanes sold by the company Goldschmidt under the names "Abilwax 9800" and "Abilwax 9801", which are poly($C_1$–$C_{20}$)alkylsiloxanes.

Among the polyalkylarylsiloxanes, mention may be made of linear and branched polymethylphenylsiloxanes, polydimethylmethylphenylsiloxanes and polydimethyldiphenylsiloxanes, such as, for example:

the oil "Rhodorsil 763" from Rhône-Poulenc, the oils "Silbione 70641 V 30 and 70641 V 200" from Rhône-Poulenc, the product "DC 556 Cosmetic Grade Fluid" from Dow Corning, the silicones of the PK series from Bayer, such as "PK20", the silicones of the PN and PH series from Bayer, such as "PN 1000" and PH 1000", certain oils of the SF series from General Electric, such as SF 1250, SF 1265, SF 1154 and SF 1023.

The silicone gums in accordance with the present invention are polydiorganosiloxanes with a molecular mass of between 200,000 and 1,000,000, used alone or as a mixture in a solvent chosen from volatile silicones, polydimethylsiloxane (PDMS) oils, polyphenylmethylsiloxane (PPMS) oils, isoparaffins, methylene chloride, pentane, dodecane, tridecane and tetradecane, or mixtures thereof.

Mention is made, for example, of the following compounds:

polydimethylsiloxane,
poly[(dimethylsiloxane)/(methylvinylsiloxane)],
poly[(dimethylsiloxane)/(diphenylsiloxane)],
poly[(dimethylsiloxane)/(phenylmethylsiloxane)],
poly[(dimethylsiloxane)/(diphenylsiloxane)/(methylvinylsiloxane)].

Mention may be made, for example, in a non-limiting manner, of the following mixtures:

1) mixtures formed from a polydimethylsiloxane hydroxylated at the end of the chain (Dimethiconol according to the CTFA nomenclature) and from a cyclic polydimethylsiloxane (Cyclomethicone according to the CTFA nomenclature), such as the product "Q2 1401" sold by the company Dow Corning;

2) mixtures formed from a polydimethylsiloxane gum with a cyclic silicone, such as the product "SF 1214

Silicone Fluid" from General Electric, which is an SE 30 gum of MW 500,000 dissolved in "SF 1202 Silicone Fluid" (decamethylcyclopentasiloxane);

3) mixtures of two PDMSs of different viscosity, in particular a PDMS gum and a PDMS oil, such as the products "SF 1236" and "CF 1241" from the company General Electric. The product "SF 1236" is a mixture of an SE 30 gum defined above, with a viscosity of 20 m²/s, and of an SF 96 oil with a viscosity of $5 \times 10^{-5}$ m²/s (15% SE 30 gum and 85% SF 96 oil). The product "CF 1241" is a mixture of an SE 30 gum (33%) and of a PDMS (67%) with a viscosity of $10^{-3}$ m²/s.

The polyorganopolysiloxane resins which can be used in accordance with the invention are preferably crosslinked siloxane systems containing the units: $R_2SiO_{2/2}$, $RSiO_{3/2}$ and $SiO_{4/2}$ in which R represents a hydrocarbon-based group having 1 to 6 carbon atoms or a phenyl group. Among these products, the ones which are particularly preferred are those in which R denotes a lower alkyl radical or a phenyl radical.

Among these resins, mention may be made of the product sold under the name "Dow Corning 593" or those sold under the names "Silicone Fluid SS 4230" and Among these resins, mention may be made of the product sold under the name "Dow Corning 593" or those sold under the names "Silicone Fluid SS 4230" and "SS 4267" by the company General Electric and which are dimethyl/trimethylpolysiloxanes.

The organomodified silicones in accordance with the present invention are silicones as defined above, containing in their general structure one or more organofunctional groups directly attached to the siloxane chain or attached via a hydrocarbon-based radical.

Mention is made, for example, of silicones containing:
a) polyethyleneoxy and/or polypropyleneoxy groups, optionally containing alkyl groups, such as:
the product known as dimethiconecopolyol sold by the company Dow Corning under the name "DC 1248", and alkyl (C12) methiconecopolyol sold by the company Dow Corning under the name "Q2 5200",
the oils "Silwet" L 722, L 7500, L 77 and L 711 from the company Union Carbide,
the mixture of dimethiconecopolyol and of cyclomethicone, such as the product sold under the name "Q2-3225C" by the company Dow Corning;
the product "Mirasil DMCO" sold by Rhône-Poulenc;
b) (per)fluoro groups, for instance trifluoroalkyl groups, such as, for example, those sold by the company General Electric under the names "FF.150 Fluorosilicone Fluid" or by the company Shin Etsu under the names "X-22-819", "X-22-820", "X-22-821", "X-22-822" or "FL 100";
c) hydroxyacylamino groups, such as those described in European patent application EP-A-0,342,834, and in particular the silicone sold by the company Dow Corning under the name "Q2-8413";
d) thiol groups, such as in the silicones "X 2-8360" from Dow Corning or "GP 72A" and "GP 71" from Genesee; Union Carbide or the silicone known as "Amodimethicone" in the CTFA dictionary;
f) carboxylate groups, such as the products described in European patent EP 186,507 from Chisso Corporation;
g) hydroxylated groups, such as the polyorganosiloxanes containing a hydroxyalkyl function, described in patent application FR-A-2,589,476, and in particular polyorganosiloxanes containing a γ-hydroxy-propyl function;
h) alkoxylated groups containing at least 12 carbon atoms, such as the product "Silicone Copolymer F 7551" from SWS Silicones and the products "Abilwax 2428", "Abilwax 2434" and "Abilwax 2440" from the company Goldschmidt;
i) acyloxyalkyl groups containing at least 12 carbon atoms, such as, for example, the poly-organosiloxanes described in patent application FR-A-2,641,185, and in particular polyorganosiloxanes containing a stearoyloxypropyl function;
j) quaternary ammonium groups, such as in the products "X2 81 08" and "X2 81 09" and the product "Abil K 3270" from the company Goldschmidt;
k) amphoteric or betaine groups, such as in the product sold by the company Goldschmidt under the name "Abil B 9950";
l) bisulphite groups, such as in the products sold by the company Goldschmidt under the names "Abil S 201" and "Abil S 255".

The block copolymers having a polysiloxane-polyoxyalkylene linear block as repeating unit, which are used in the context of the present invention, preferably have the following general formula:

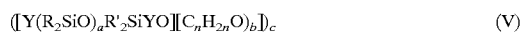  (V)

in which
R and R', which may be identical or different, represent a monovalent hydrocarbon-based radical containing no aliphatic unsaturation,
n is an integer ranging from 2 to 4,
a is an integer greater than or equal to 5, preferably between 5 and 200 and even more particularly between 5 and 100,
b is an integer greater than or equal to 4, preferably between 4 and 200 and even more particularly between 5 and 100,
c is an integer greater than or equal to 4, preferably between 4 and 1000 and even more particularly between 5 and 300,
Y represents a divalent organic group which is linked to the adjacent silicon atom via a carbon-silicon bond and to a polyoxyalkylene block via an oxygen atom,
the average molecular weight of each siloxane block is between about 400 and about 10,000, that of each polyoxyalkylene block being between about 300 and about 10,000,
the siloxane blocks represent from about 10% to about 95% of the weight of the block copolymer,
the average molecular weight of the block copolymer being at least 3000 and preferably between 5000 and 1,000,000 and even more particularly between 10,000 and 200,000.

R and R' are preferably chosen from the group comprising alkyl radicals such as, for example, the methyl, ethyl, propyl, butyl, pentyl, hexyl, octyl, decyl and dodecyl radicals, aryl radicals such as, for example, phenyl and naphthyl, aralkyl radicals such as, for example, benzyl and phenethyl, and tolyl, xylyl and cyclohexyl radicals.

Y is preferably —R"—, —R"—CO—, —R"—NHCO—, —R"—NH—CO—NH—R"—NHCO or —R"—OCONH—R'"—NHCO—, where R" is a divalent alkylene group such as, for example, ethylene, propylene or butylene, and R'" is a divalent alkylene group or a divalent arylene group such as —$C_6H_4$—, —$C_6H_4C_6H_4$—, $C_6H_4$—$CH_2$—$C_6H_4$, $C_6H_4$—$C(CH_3)_2$—$C_6H_4$—.

Even more preferably, Y represents a divalent alkylene radical, more particularly the —$CH_2$—$CH_2$—$CH_2$— radical or the —$C_4H_8$— radical.

The preparation of the block copolymers used in the context of the present invention is described in European application EP 0,492,657 A1, the teaching of which is included by way of reference in the present description.

The preferred polysiloxane-polyoxyalkylene linear block copolymers according to the invention are chosen from those of formula:

$$[C_4H_8O(C_nH_{2n}O)_b(C_mH_{2m}O)_d\text{—}C_4H_8\text{—}SiMe_2O(SiMe_2)_aSiMe_2(VI)$$

where Me represents methyl, n and m are integers ranging from 2 to 4, a is an integer greater than or equal to 4, or preferably between 5 and 200, b and d are integers greater than or equal to 0, preferably between 4 and 200, b+d is greater than or equal to 4, preferably between 4 and 200, and c is an integer greater than or equal to 4, preferably between 4 and 1000.

Among these copolymers, the ones more particularly used are those having a repeating unit of formula:

$$[\text{—}(SiMe_2O)_xSiMe_2\text{—}C_4H_8O\text{—}(C_2H_4O)_y\text{—}(C_3H_6O)_z\text{—}C_4H_8\text{—}(VII)$$

where x is a number between 5 and 15 (limits included), y is a number between 15 and 30 (limits included), and z is a number between 20 and 40 (limits included).

Among these polymers, the ones more particularly used are those in which the siloxane/polyoxyalkylene weight ratio is about 20 and the polyoxyethylene/polyoxypropylene weight ratio is about 65/35.

Polymers can also be chosen in which the repeating unit is of formula (VI) and whose siloxane/polyoxyalkylene weight ratio is about 75 and whose polyoxyethylene/polyoxypropylene weight ratio is about 50/50, polymers whose siloxane/polyoxyalkylene weight ratio is about 35 and whose polyoxyethylene/polyoxypropylene weight ratio is about 100/0, and polymers whose siloxane/polyoxyalkylene weight ratio is about 30 and whose polyoxyethylene/polyoxypropylene weight ratio is about 0/100.

According to a particular embodiment of the invention, the block copolymer is chosen from the following copolymers:

[[(CH$_3$)$_2$SiO]$_{41}$(CH$_3$)$_2$SiCH$_2$

CH(CH$_3$)CH$_2$—O(C$_2$H$_4$O)$_{18}$

—(C$_3$H$_6$O)$_{33}$CH$_2$CH(CH$_3$)CH$_2$]

$_{16.1}$[[(CH$_3$)$_2$SiO]$_{31}$ (CH$_3$)$_2$SiCH$_2$CH(CH$_3$)CH$_2$

—O(C$_2$H$_4$O)$_{20}$—(C$_3$H$_6$O)$_{29}$

CH$_2$CH(CH$_3$)CH$_2$]$_{13.3}$

[[(CH$_3$)$_2$SiO]$_9$(CH$_3$)$_2$

SiCH$_2$CH(CH$_3$)CH$_2$

—O(C$_2$H$_4$O)$_{20}$—(C$_3$H$_6$O)$_{29}$

CH$_2$CH(CH$_3$)CH$_2$]$_{26.3}$

[[(CH$_3$)$_2$SiO]$_{16}$(CH$_3$)$_2$

SiCH$_2$CH(CH$_3$)CH$_2$—O(C$_2$

H$_4$O)$_{18}$—(C$_3$H$_6$O)$_{20}$CH$_2$

CH(CH$_3$)CH$_2$]$_{21.5}$

[[(CH$_3$)$_2$SiO]$_9$(CH$_3$)$_2$

SiCH$_2$CH(CH$_3$)CH$_2$

—O(C$_2$H$_4$O)$_5$—CH$_2$

CH(CH$_3$)CH$_2$]$_{4.8}$

The polymers containing a non-silicone organic skeleton grafted with monomers containing a polysiloxane, in accordance with the invention, are preferably chosen from those described in U.S. Pat. Nos. 4,963,935, 4,728,571 and 4,972,037 and patent applications EP-A-0,412,704, EP-A-0,412,707, EP-A-0,640,105 and WO 95/00578, the teachings of which are included in their entirety in the present description by way of non-limiting references. They are copolymers obtained by radical polymerization from monomers containing ethylenic unsaturation and from silicone macromonomers having a vinyl end group, or alternatively copolymers obtained by reaction of a polyolefin comprising functionalized groups and of a polysiloxane macromer having an end function which is reactive with the said functionalized groups.

Examples of polymers containing a polysiloxane skeleton grafted with non-silicone organic monomers, which are suitable for carrying out the present invention, as well as the particular method for preparing them, are described in particular in patent applications EP-A-0,582,152, WO 93/23009 and WO 95/03776, the teachings of which are included in their entirety in the present description by way of non-limiting references.

The polyorganosiloxanes preferably used according to the invention are non-volatile polyorgano-polysiloxanes.

The polyorganosiloxanes are used in the compositions of the invention in proportions of between 0.01 and 50% by weight, and preferably between 0.1 and 30% by weight relative to the total weight of the composition.

The compositions according to the invention contain a cosmetically acceptable aqueous medium. They have a pH which can range from 3.5 to 11, preferably between 5.5 and 11 and even more preferably between 5.5 and 8.5.

The cosmetically acceptable medium for the compositions according to the invention consists more particularly of water and optionally of cosmetically acceptable organic solvents.

The organic solvents can represent from 0.5 to 90% of the total weight of the composition. They can be chosen from the group consisting of hydrophilic organic solvents, lipophilic organic solvents, amphiphilic solvents or mixtures thereof.

Among the hydrophilic organic solvents, mention may be made, for example, of linear or branched lower monoalcohols having from 1 to 8 carbon atoms, polyethylene glycols having from 6 to 80 ethylene oxide units, and polyols.

As amphiphilic organic solvents, mention may be made of polypropylene glycol (PPG) derivatives, such as esters of polypropylene glycol and of fatty acid, derivatives of PPG and of fatty alcohol, such as PPG-23 oleyl ether, and PPG-36 oleate.

As lipophilic organic solvents, mention may be made, for example, of fatty esters such as diisopropyl adipate, dioctyl adipate, alkyl benzoates and dioctyl malate.

In order for the cosmetic compositions of the invention to be more pleasant to use (softer when applied, more nourishing and more emollient), it is possible to add a fatty phase to the medium of these compositions.

The fatty phase can represent up to 50% of the total weight of the composition.

This fatty phase can contain an oil or a wax or mixtures thereof, and can also comprise fatty acids, fatty alcohols and fatty acid esters. The oils can be chosen from animal, plant, mineral or synthetic oils and in particular from liquid petroleum jelly, liquid paraffin, isoparaffins, poly-α-olefins, fluoro oils and perfluoro oils. Similarly, the waxes can be chosen from animal, fossil, plant, mineral or synthetic waxes which are known per se.

The compositions of the invention can contain adjuvants that are common in the cosmetics field, such as other standard gelling agents and/or thickeners; emulsifiers; surfactants; moisturizers; emollients; sunscreens; hydrophilic or lipophilic active agents such as ceramides; anti-free-radical agents; sequestering agents; antioxidants; preserving agents; acidifying or basifying agents; fragrances; fillers; dyestuffs; reducing agents. The amounts of these various additives are those used conventionally in the fields considered.

Needless to say, a specialist will take care to select the optional compound(s) to be added to the composition according to the invention such that the advantageous properties intrinsically associated with the composition in accordance with the invention are not, or are not substantially, adversely affected by the addition envisaged.

The compositions according to the invention can be in any form which is suitable for topical application, in particular in the form of lotion-type solutions, in the form of aqueous or aqueous-alcoholic gels, in the form of vesicle dispersions or in the form of simple or complex emulsions (O/W, W/O, O/W/O or W/O/W emulsions) and can be of liquid, semi-liquid or solid consistency, such as milks, creams, gels, cream-gels, pastes and sticks, and can optionally be packaged as an aerosol and can be in the form of mousses or sprays. These compositions are prepared according to the usual methods.

The compositions according to the invention are preferably used as rinse-out or leave-in hair products, in particular to wash, dye, care for, condition, straighten or maintain the hairstyle or to permanently or temporarily reshape the hair.

The compositions can be styling products such as hair-setting lotions, blow-drying lotions, fixing compositions and styling compositions. The lotions can be packaged in various forms, in particular in vaporizers, pump-dispenser bottles or in aerosol containers in order to ensure application of the composition in vaporized form or in the form of a mousse. Such packaging forms are indicated, for example, when it is desired to obtain a spray or a mousse for fixing or treating the hair.

The compositions of the invention can also be shampoos, rinse-out compositions or leave-in compositions, to be applied before or after shampooing, dyeing, bleaching, permanent-waving or straightening the hair.

The compositions of the invention can also be used as hygiene or care products, such as protective, treatment or beauty creams for the face, for the hands or for the body, protective or care body milks, and skincare or skin cleansing lotions, gels or mousses.

The compositions of the invention can also be used as antisun compositions.

The compositions can also consist of solid preparations constituting cleansing soaps or bars.

The compositions of the invention can also be used as oral care products such as toothpastes and mouthwashes.

The compositions can be make-up products such as face creams, foundations, mascaras, eyeliners, lipsticks or nail varnishes.

Another subject of the invention is a cosmetic, non-therapeutic treatment process for the skin, the scalp, the hair, the eyelashes, the eyebrows, the nails or mucous membranes, characterized in that a composition as defined above is applied to the keratinous support, according to the usual technique for using this composition, for example application of creams, gels, sera, lotions or milks to the skin, the scalp or mucous membranes.

The examples which follow illustrate the invention without being limiting in nature.

EXAMPLE 1

Shampoo

| | |
|---|---|
| Sodium lauryl ether sulphate containing 2.2 mol of ethylene oxide | 17 g AM |
| Cocoylbetaine | 2.8 g AM |
| Ethoxylated methacrylic acid/methyl acrylate/behenyl dimethylmetaisopropenyl-benzyl isocyanate terpolymer (40 EO), as an aqueous 25% dispersion | 1 g AM |
| Polydimethylsiloxane of molecular mass 250,000 and of viscosity 0.5 m²/s, sold under the name "Mirasil DM 500,000" by Rhône-Poulenc | 2.5 g |
| Water qs pH adjusted to 6.5 (NaOH) | 100 g |

This shampoo has the appearance of a thickened liquid which is stable after one week at room temperature. It has good foaming properties and leaves the hair soft after shampooing.

Comparative Example 2

Shampoo

| | |
|---|---|
| Sodium lauryl ether sulphate containing 2.2 mol of ethylene oxide | 17 g AM |
| Cocoylbetaine | 2.8 g AM |
| Polyurethane containing a polyethoxylated alkyl end, as a solution at 35% in a propylene glycol/water mixture (60/40) ("Acrysol 44" sold by the company Rohm & Haas) | 1 g AM |
| Polydimethylsiloxane of molecular mass 250,000 and of viscosity 0.5 m²/s, sold under the name "Mirasil DM 500,000" by Rhône-Poulenc | 2.5 g |
| Water qs pH adjusted to 6.5 (NaOH) | 100 g |

This shampoo has the appearance of an unstable, thickened, cloudy liquid which settles out into separate phases after one week at room temperature.

EXAMPLE 3

Leave-in Haircare Gel

| | |
|---|---|
| Ethoxylated methacrylic acid/methyl acrylate/behenyl dimethylmetaisopropenyl-benzyl isocyanate terpolymer (40 EO), as an aqueous 25% dispersion | 1 g AM |

| | |
|---|---|
| Polydimethylsiloxane of molecular mass 250,000 and of viscosity 0.5 m²/s, sold under the name "Mirasil DM 500,000" by Rhône-Poulenc | 1 g |
| 2-Amino-2-methyl-1-propanol (AMP), qs pH adjusted to 7.5 | |
| Fragrance, preserving agent, dye qs | |
| Demineralized water qs | 100 g |

A non-pasty, thick, stable gel which spreads well on the hair is obtained. This gel gives the hair a soft feel and good disentangling ability and has good fixing properties.

If the above terpolymer is replaced with the polyurethane "Acrysol 44" used in Comparative Example 2, an unstable, cloudy, non-gelled, thickened liquid is obtained.

If the terpolymer is replaced with the crosslinked acrylic acid/$C_{10}$/$C_{30}$ alkyl acrylate copolymer "Pemulen TR1" sold by Goodrich, a pasty gel which does not spread very well and which gives the hair mediocre properties of softness and disentangling is obtained.

EXAMPLE 4

Leave-in Haircare Gel

| | |
|---|---|
| Ethoxylated methacrylic acid/methyl acrylate/behenyl dimethylmetaisopropenyl-benzyl isocyanate terpolymer (40 EO), as an aqueous 25% dispersion | 1 g AM |
| Polydimethylsiloxane of viscosity 5 × 10⁻⁵ m²/s sold under the name "Mirasil DM 50" by Rhône-Poulenc | 1 g |
| 2-Amino-2-methyl-1-propanol (AMP), qs pH adjusted to 7.5 | |
| Fragrance, preserving agent, dye qs | |
| Demineralized water qs | 100 g |

A non-pasty, thick, stable gel which spreads well on the hair is obtained. This gel gives the hair a soft feel and good disentangling ability and has good fixing properties.

If the above terpolymer is replaced with the polyurethane "Acrysol 44" used in Comparative Example 2, an unstable, cloudy, non-gelled, thickened liquid is obtained.

If the terpolymer is replaced with the crosslinked acrylic acid/$C_{10}$/$C_{30}$ alkyl acrylate copolymer "Pemulen TR1" sold by Goodrich, a pasty gel is obtained which does not spread very well and which gives the hair mediocre softness properties; it also has poor fixing properties.

EXAMPLE 5

Leave-in Haircare Gel

| | |
|---|---|
| Ethoxylated methacrylic acid/methyl acrylate/behenyl dimethylmetaisopropenyl-benzylisocyanate terpolymer (40 EO), as an aqueous 25% dispersion | 1 g AM |
| Oxyethylenated and oxypropylenated polydimethylsiloxane of viscosity 1.5 ± 0.2 × 10⁻³ m²/s, sold under the name "Mirasil DMCO" by Rhône-Poulenc | 1 g |
| 2-Amino-2-methyl-1-propanol (AMP), pH adjusted to 7.5 qs | |
| Fragrance, preserving agent, dye qs | |
| Demineralized water qs | 100 g |

A non-pasty, thick, stable gel which spreads well on the hair is obtained. This gel gives the hair a soft feel and good disentangling ability and has good fixing properties.

If the above terpolymer is replaced with the polyurethane "Acrysol 44" used in Comparative Example 2, an unstable, cloudy, non-gelled, thickened liquid is obtained.

If the terpolymer is replaced with the crosslinked acrylic acid/$C_{10}$/$C_{30}$ alkyl acrylate copolymer "Pemulen TR1" sold by Goodrich, a pasty gel is obtained which does not spread very well and which gives the hair very mediocre softness and disentangling properties; it also has poor fixing properties.

EXAMPLE 6

High-protection Sun Cream-gel

| | |
|---|---|
| 4-tert-Butyl-4'-methoxydibenzoylmethane ("Parsol 1789" sold by the company Roche) | 2 g |
| Benzene-1,4-di(3-methylidene-10-camphorsulphonic acid) as an aqueous 33% solution | 1.5 g |
| 2-Ethylhexyl 2-cyano-3,3-diphenylacrylate ("Uvinul N 539" sold by the company BASF) | 10 g |
| Ethoxylated methacrylic acid/methyl acrylate/behenyl dimethylmetaisopropenyl benzyl isocyanate terpolymer (40 EO), as an aqueous 25% dispersion | 3 g AM |
| Oxyethylenated and oxypropylenated polydimethyl/methylsiloxane, at 10% in D4/D5 | 1 g AM |
| Cyclohexadimethylsiloxane | 5 g |
| Isohexadecane | 10 g |
| 12-Hydroxystearic acid oligomer stearate | 0.5 g |
| Moisturizers | 8 g |
| Sequestering agent qs | |
| Triethanolamine qs pH 7 | |
| Sterilized demineralized water qs | 100 g |

A homogeneous, stable cream-gel which spreads well on the skin is obtained.

What is claimed is:

1. Cosmetic composition for treating keratinous material, in a cosmetically acceptable aqueous at least one polyorganosiloxane and an acrylic terpolymer comprising:
   a) about 20 to 70% by weight, of a carboxylic acid containing α,β-monoethylenic unsaturation;
   b) about 20 to 80% by weight, of a non-surfactant monomer containing monoethylenic unsaturation, which is different from a); and
   c) about 0.5 to 60% by weight, of a nonionic urethane monomer which is the product of reaction of a monohydric nonionic surfactant with a monoisocyanate containing monoethylenic unsaturation.

2. Composition according to claim 1, wherein the carboxylic acid containing α,β-monoethylenic unsaturation a) is acrylic acid, methacrylic acid, itaconic acid or maleic acid.

3. Composition according to claim 2, wherein the carboxylic acid containing α,β-monoethylenic unsaturation a) is methacrylic acid.

4. Composition according to claim 1, wherein the non-surfactant monomer containing monoethylenic unsaturation b) is $C_1$–$C_4$ alkyl acrylates or methacrylates, styrene, vinyltoluene, vinyl acetate, acrylonitrile or vinylidene chloride.

5. Composition according to claim 4, wherein the non-surfactant monomer containing monoethylenic unsaturation is methyl or ethyl acrylate.

6. Composition according to claim 1, wherein the monohydric nonionic surfactant used to obtain the nonionic urethane monomer c) has the formula:

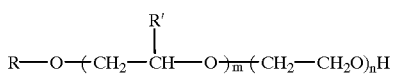

in which R is a $C_6$–$C_{30}$ alkyl or $C_8$–$C_{30}$ aralkyl group, R' is a $C_1$–$C_4$ alkyl group, n is an average number ranging from about 5 to 150 and m is an average number ranging from about 0 to 50, with the condition that n is at least as large as m and that n+m=5–150.

7. Composition according to claim 6, wherein R is a dodecyl, $C_{18}$–$C_{26}$ alkyl or ($C_8$–$C_{13}$)alkylphenyl group, m=0 and n is an average number ranging approximately from 5 to 150.

8. Composition according to claim 1, wherein the monoisocyanate containing monoethylenic unsaturation used to form the nonionic urethane monomer c) is α,α-dimethyl-m-isopropenyl-benzyl isocyanate.

9. Composition according to claim 1, wherein the acrylic terpolymer is an aqueous dispersion obtained from methacrylic acid as component a), methyl acrylate as component b) and a nonionic urethane macromonomer of the following structure:

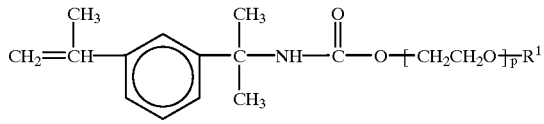

in which p ranges from 6 to 150 and $R^1$ is a $C_{18}$–$C_{26}$ alkyl radical.

10. Composition according to claim 1, wherein the acrylic terpolymer is present in concentrations ranging from 0.01 to 20% by weight relative to the total weight of the composition.

11. Composition according to claim 1, wherein the polyorganosiloxanes are cyclic volatile silicones containing 3 to 7 silicon atoms and having a boiling point of between 60° C. and 260° C.

12. Composition according to claim 1, wherein the polyorganosiloxanes are non-volatile silicones selected from the group consisting of:
  (i) polyalkylsiloxanes;
  (ii) polyarylsiloxanes;
  (iii) polyalkylarylsiloxanes;
  (iv) silicone gums;
  (v) silicone resins;
  (vi) organomodified polyorganosiloxanes containing, in their general structure, one or more organofunctional groups directly attached to the siloxane chain or attached via a hydrocarbon-based radical;
  (vii) block copolymers having a polysiloxanepolyalkylene linear block as repeating unit;
  (viii) grafted silicone polymers containing a non-silicone organic skeleton, consisting of an organic main chain formed from organic monomers not containing silicone, onto which is grafted, within the said chain as well as, optionally, on at least one of its ends, at least one polysiloxane macromonomer;
  (ix) grafted silicone polymers containing a polysiloxane skeleton, grafted with non-silicone organic monomers, comprising a polysiloxane main chain onto which is grafted, within the said chain as well as, optionally, on at least one of its ends, at least one organic macromonomer containing no silicone;
  (x) and mixtures thereof.

13. Composition according to claim 12, wherein the polyalkylsiloxanes are selected from the group consisting of:
  linear polydimethylsiloxanes containing trimethylsilyl end groups, and
  linear polydimethylsiloxanes containing hydroxydimethylsilyl end groups.

14. Composition according to claim 12, wherein the silicone gums are polydiorganosiloxanes with a molecular mass of between 200,000 and 1,000,000, used alone or as a mixture in a solvent chosen from volatile silicones, polydimethylsiloxane (PDMS) oils, polyphenylmethylsiloxane (PPMS) oils, isoparaffins, methylene chloride, pentane, dodecane, tridecane or tetradecane, or mixtures thereof.

15. Composition according to claim 14, wherein the silicone gums are:
  polydimethylsiloxane,
  poly[(dimethylsiloxane)/(methylvinylsiloxane)],
  poly[(dimethylsiloxane)/(diphenylsiloxane)],
  poly[(dimethylsiloxane)/(phenylmethylsiloxane)], or
  poly[(dimethylsiloxane)/(diphenylsiloxane)/(methylvinylsiloxane)].

16. Composition according to claim 14, wherein the silicone gums are selected from the group consisting of:
  a) mixtures formed from a polydimethylsiloxane which is hydroxylated at the end of the chain and from a cyclic polydimethylsiloxane;
  b) mixtures formed from a polydimethylsiloxane gum with a cyclic silicone; and
  c) mixtures of two polydimethylsiloxanes of different/viscosity.

17. Composition according to claim 12, wherein the polyorganosiloxane resins are crosslinked siloxane systems containing the units:
  $R_2SiO_{2/2}$, $RSiO_{3/2}$ and $SiO_{4/2}$ in which R represents a hydrocarbon-based group having 1 to 6 carbon atoms or a phenyl group.

18. Composition according to claim 12, wherein the organomodified polyorganosiloxanes are chosen from those containing:
  a) polyethyleneoxy and/or polypropyleneoxy groups, optionally containing alkyl groups;
  b) (per)fluoro groups;
  c) hydroxyacylamino groups;
  d) thiol groups;
  e) carboxylate groups;
  f) hydroxylated groups;
  h) alkoxylated groups;
  i) acyloxyalkyl groups;
  j) substituted or unsubstituted amine groups;
  k) quaternary ammonium groups;

l) amphoteric or betaine groups; or m) bisulphite groups.

19. Composition according to claim 12, wherein in that the polysiloxane-polyoxyalkylene linear block copolymer corresponds to the general formula:

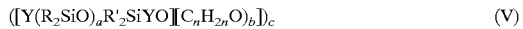  (V)

in which

R and R', which may be identical or different, represent a monovalent hydrocarbon-based radical containing no aliphatic unsaturation, n is an integer ranging from 2 to 4, a is an integer greater than or equal to 5, b is an integer greater than or equal to 4, c is an integer greater than or equal to 4, Y represents a divalent organic group which is linked to the adjacent silicon atom via a carbon-silicon bond and to a polyoxyalkylene block via an oxygen atom, the average molecular weight of each siloxane block is between about 400 and about 10,000, that of each polyoxyalkylene block being between about 300 and about 10,000, the siloxane blocks representing from about 10% to about 95% of the weight of the block copolymer, the average molecular weight of the block copolymer being at least 3000.

20. Composition according to claim 1, wherein the polyorganosiloxanes is are present in concentrations ranging from 0.01 to 50% by weight relative to the total weight of the composition.

21. Composition according to claim 1, wherein the composition it has a pH ranging from 3.5 to 11.

22. Composition according to claim 1, wherein the cosmetically acceptable aqueous medium consists of water or of water and at least one organic solvent chosen from the group consisting of hydrophilic, lipophilic and amphiphilic organic solvents, and mixtures thereof.

23. Composition according to claim 1, further comprising at least one fatty substance, gelling agent and/or thickener, surfactant, moisturizer, emollient, sunscreen, hydrophilic or lipophilic active agent, anti-free-radical agent, sequestering agent, antioxidant preserving agent, basifying or acidifying agent, fragrance, filler, dyestuff or reducing agent.

24. Composition according to claim 1, wherein the composition it is in the form of an emulsion, a lotion, a gel, a vesicle dispersion, a paste or a solid tube or is packaged as an aerosol and is in the form of a mousse or a spray.

25. Composition according to claim 1, wherein the composition it is a rinse-out or leave-in hair product to wash, dye, care for, condition, straighten or maintain the hairstyle or to permanently or temporarily reshape the hair, an antisun product, an oral care product or a make-up product.

26. Cosmetic, non-therapeutic treatment process for protecting keratinous material comprising applying an effective amount of a composition as defined in claim 1 to the keratinous material.

27. Composition according to claim 1, wherein the acrylic terpolymer comprises about 25 to 55% by weight of the carboxylic acid containing α,β-monoethylenic unsaturation, about 30 to 65% by weight of the non-surfactant monomer containing monoethylenic unsaturation and about 10 to 50% by weight of the nonionic urethane monomer.

28. Composition according to claim 9, wherein R' is a linear $C_{20}$–$C_{24}$ alkyl radical of plant origin.

29. Composition according to claim 28, wherein the alkyl radical of plant origin is the docosyl radical.

30. Composition according to claim 10, wherein the concentration of acrylic terpolymer is from 0.1 to 10% by weight.

31. Composition according to claim 20, wherein the concentration of the polyorganosiloxanes is from 0.1 to 30% by weight.

32. Composition according to claim 21, wherein the pH range is from 5.5 to 8.5.

33. Process according to claim 26, wherein the keratinous material is skin, hair, eyelashes, eyebrows or mucous membranes.

* * * * *